United States Patent [19]
Johnson

[11] Patent Number: 4,816,021
[45] Date of Patent: Mar. 28, 1989

[54] SELF-DESTRUCTING HYPODERMIC SYRINGES AND HYPODERMIC PLUNGER DEVICES

[76] Inventor: Scott A. Johnson, c/o Lois Johnson, 113 Grand Ave., Ottumwa, Iowa 52501

[21] Appl. No.: 29,781

[22] Filed: Mar. 25, 1987

[51] Int. Cl.$^4$ .............................................. A61M 5/00
[52] U.S. Cl. ..................................... 604/110; 604/187
[58] Field of Search ................................ 604/110, 187

[56] References Cited
U.S. PATENT DOCUMENTS 2,484,290 10/1949 Handel ................................ 604/110
4,252,118 2/1981 Richard et al. ..................... 604/110

Primary Examiner—Larry Jones
Assistant Examiner—Noah Kamen

[57] ABSTRACT

A self-destructing hypodermic device to allow one-time use only of the device. The device includes a syringe casing, a syringe tip, and a syringe plunger; all cooperating and functioning to allow solutions or medications to be drawn into the casing, and then intravenously injected into a user. At least some part or portion of the casing, plunger, and tip is comprised of a material which self destructs, at least partially, upon contact with the medication or solution intravenously injected, rendering the device unusable after one use. In one embodiment, the self-destructing portion of the casing, plunger, or tip is comprised of a material which is at least partially soluble in the medications or solutions intravenously injected by the device. Optionally, a tip cover can be used which can grip the syringe tip after use, to assist in disabilitating the device after one use.

18 Claims, 1 Drawing Sheet

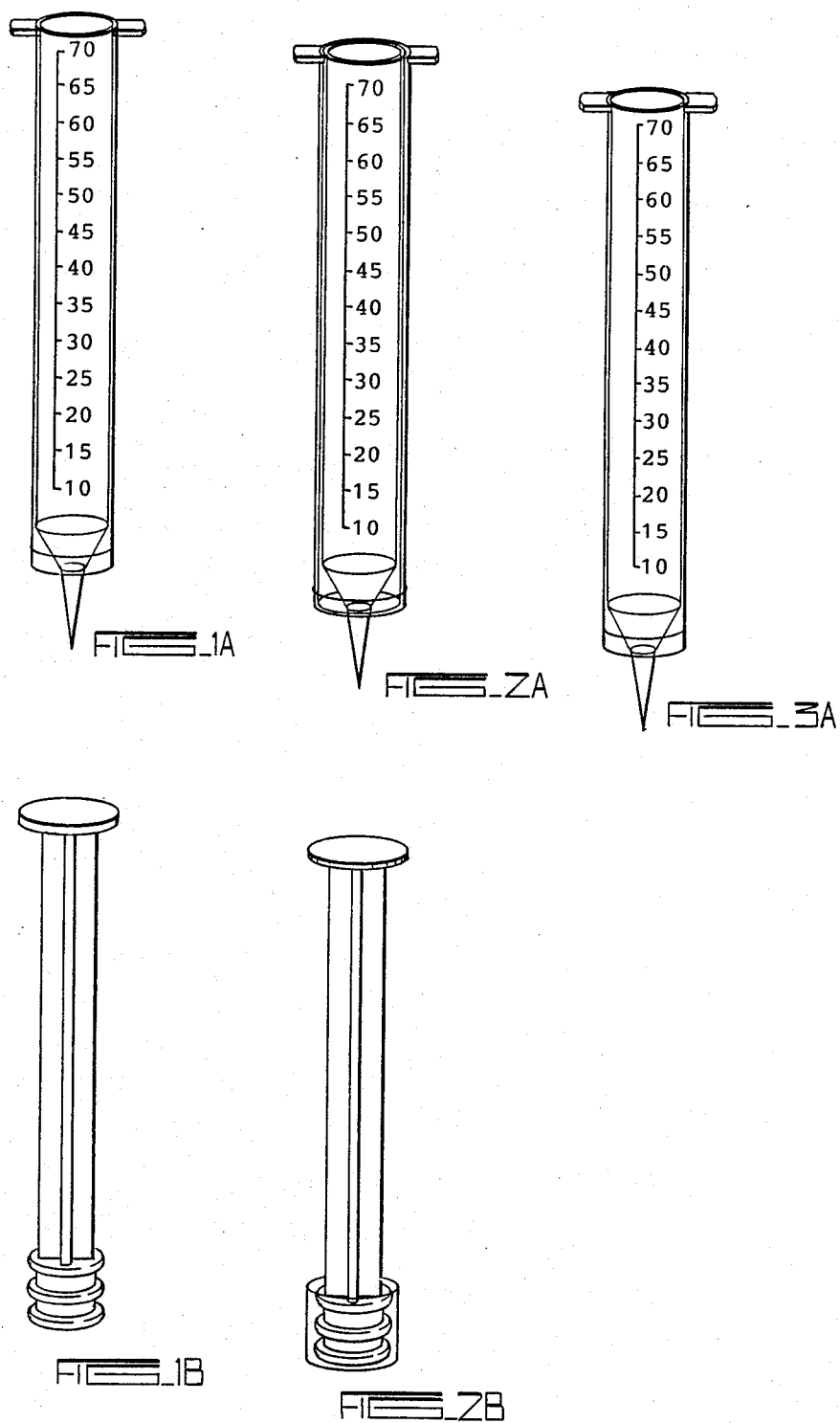

SELF-DESTRUCTING HYPODERMIC SYRINGES AND HYPODERMIC PLUNGER DEVICES

BACKGROUND OF THE INVENTION

1. Field of the Invention

This invention (self-destructing hypodermic syringes) relates in general to all hypodermic syringes and in particular hypodermic syringes that self-destruct after exposure to water and/or alcohol based medicines. The self-destructing properties of my hypodermic syringes are due to the collodion materials used; collagens suitable in water and/or alcohol.

2. Problems in the Art

Acquired immune deficiency syndrome (AIDS) is a tremendously serious health problem. A major form of transmission of the disease is believed to be common use of an infected intravenous syringe needles. Thus, if repeated use of the same hypodermic needle could be prevented, retardation of the transmission of AIDS would hopefully be accomplished.

SUMMARY OF THE INVENTION

Hypodermic syringes are a combination of syringe casings (FIGS. 1A, 2A, 3A) needle (FIGS. 1A, 2A, 3A) and plunger device so arranged that to effectively use the hypodermic syringe, the plunger device (FIGS. 1B and/or 2B) must be fit into the syringe casing to extract medicine from vials and to propel medications through the syringe and into circulatory system. The destruction of the self-destructing syringe will be initiated by the introduction of water and/or alcohol based medicines into the syringe casing. The destruction of the hypodermic syringe will be controlled by the type of collagen used and its thickness. Those trace amounts of collagen that enter the circulatory system with the intravenous injection will be broken down by the lympocytes present in the blood.

The advantage of self-destructing hypodermic syringes is that after one use the syringe is rendered useless, thus preventing the multiple usage and spread of disease from contaminated needles, i.e., AIDS. The introduction of the self-destructing syringe will save the lives of intravenous drug abusers, decrease the transmission of AIDS to sexual partners of intravenous drug abusers; while maintaining many of the favorable aspects of the old hypodermic syringes.

BRIEF DESCRIPTION OF THE DRAWINGS

FIG. 1A illustrates a hypodermic syringe casing. The syringe casing is constructed of Gelare. The needle construction of FIG. 1A displays two alternatives of material construction metal or Gelare. FIG. 2A illustrates a hypodermic syringe casing. The syringe casing is a lamination of a plastic exterior with an interior coating of Gelare. The needle tip construction of FIG. 2A utilizes the construction alternative described as in FIG. 1A.

FIG. 3A illustrates a hypodermic syringe casing constructed entirely of plastic or the lamination procedure described in FIG. 2A. The needle construction of 3A will utilize the alternative materials suggested for FIGS. 1A and/or 2A.

FIG. 1B is an illustration of the hypodermic syringe plunger device. The construction material for the plunger device of FIG. 1B is to be plastic with a rubber tip and/or Gelare with a rubber tip.

FIG. 2B is an illustration of the hypodermic syringe plunger device. The material construction of the device houses those alternatives mentioned in FIG. 1B with the addition of a self-detaching Gelare cap attached to the rubber tip.

DETAILED DESCRIPTION OF THE PREFERRED EMBODIMENTS

For the purpose of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated devices, and such further application of the principles of the invention as illustrated therein being contemplated as would normally occur to one skilled in the art to which the invention relates. Hypodermic syringes are combinations of syringe casings (FIGS. 1A, 2A and/or 3A), hypodermic needles (FIGS. 1A, 2A and/or 3A) and plunger devices (FIGS. 1B and/or 2B) so arranged that to effectively use the hypodermic syringe the plunger device (1B and/or 2B) must be fit into the syringe casings top opening of (1A, 2A and/or 3A) depressed completely from the to opening of the syringe casings (FIGS. 1A, 2A and/or 3A) and drawn distally from syringe bottom to selected dosage to extract medications from vials, then the plunger device (FIGS. 1B and/or 2B). thus propelling medications to enter the circulatory system. Most intravenous drugs contain water and/or alcohol. The introduction of these water and/or alcohol based drugs into the syringe casings (FIGS. 1A, 2A and/or 3A) will initiate the self-destruction of the collagen constructed syringe casings (FIGS. 1A, 2A and/or 3A), the collagen hypodermic needles (FIGS. 1A, 2A and/or 3A), and the collagen plunger devices (FIGS. 1B, and/or 2B). The descriptions of the preferred embodiments will include the hypodermic needles construction (FIGS. 1A, 2A and/or 3A) and the construction alternatives of the plunger devices (FIGS. 1B and/or 2B) as they interact and relate with the syringe casings (FIGS. 1A, 2A and/or 3A).

The syringe casing (FIG. 1A) is composed entirely of collagen materials soluble in water and/or alcohol and houses the hypodermic needle. As described in (FIGS. 1A, 2A and/or 3A), the hypodermic needle is constructed of the traditional metal, as in the current hypodermic needled syringes, or it may be constructed of collodion materials. The plunger devices (FIGS. 1B and/or 2B) may be constructed entirely of plastic with a rubber tip or the plunger devices may be constructed of the collagen materials suggested for the construction of the syringe casing (FIG. 1A) and rubber tipped.

After the syringe casing (FIG. 1A) has been exposed to the water and/or alcohol based medication and the drugs have been administered to the patient, the syringe casing (FIG. 1A), the hypodermic needle (FIGS. 1A, 2A and/or 3A) and the collagen constructed plunger devices (FIGS. 1B and/or 2B) self-destruct. If the plunger device (FIG. 2B) is utilized with the syringe casing (FIG. 1A), the self-detaching Gelare cap will separate from the plunger device (FIG. 2B) and obstruct the existing opening between the syringe casing (FIG. 1A) and the hypodermic needles of (FIGS. 1A, 2A and/or 3A). The option of the plunger device (FIG. 2B) with the Gelare cap is a precautionary measure to an incomplete destruction of the syringe casing (FIG. 1A).

The syringe casing (FIG. 2A) is a lamination of a plastic exterior with an interior coating/sleeve of Gelare with the Gelare coating/sleeve housing the hypodermic needle (FIGS. 1A, 2A and/or 3A). The hypodermic needle construction (FIGS. 1A, 2A and/or 3A) utilizes the material construction alternatives described in (FIG. 1A). The plunger devices (FIGS. 1B and/or 2B) may be constructed entirely of plastic with a rubber tip or constructed of the collagen suggested for the construction for the syringe casing in (FIG. 1A). The plunger devices of (FIGS. 1B and/or 2B) would be smaller in diameter than those utilized in the syringe casings of (FIGS. 1A and/or 3A). The decrease in plunger devices diameter (FIG. 1B and/or 2B) when coupled with syringe casing (FIG. 2A) is to account for the Gelare coating/sleeve.

After the syringe casing (FIG. 2A) has been exposed to the water and/or alcohol based medications and the drug has been administered to the patient, the Gelare coating/sleeve (FIG. 2A), the collodion hypodermic needle (FIGS. 1A, 2A and/or 3A) and the collagen constructed plunger devices (FIGS. 1B and/or 2B) self-destruct leaving the exterior plastic syringe casing (FIG. 2A) remaining solid and useless. The plunger device (FIG. 2B) with the Gelare self-detaching cap may be used with the syringe casing (FIG. 2A). The Galare cap will separate from the plunger device (FIG. 2B) and obstruct the existing opening through the syringe casing (FIGS. 1A, 2A and/or 3A) to the hypodermic needles (FIGS. 1A, 2A and/or 3A). The option of the Gelare capped plunger device (FIG. 2B) is a precautionary measure to an incomplete destruction of the Gelare coating/sleeve of (FIG. 2A).

The syringe casing of (FIG. 3A) will be constructed of plastic with a Gelare tip (FIG. 3A) housing the hypodermic needle. The hypodermic needle (FIG. 1A, 2A and/or 3A) will be constructed of the traditional metal and/or composed of a collagen material. The plunger devices (FIG. 1B and/or 2B) will be constructed entirely of plastic or constructed of the same collodion material used in the construction of the syringe casing of (FIG. 1A and 2A).

After the plastic syringe casing of FIG. 3A has been exposed to water and/or alcohol based medicines and the medication has been administered to the patient, the Gelare tip of (FIG. 3A) will self-destruct freeing the metal or collodion hypodermic needle (FIGS. 1A, 2A and/or 3A) from the plastic syringe casing (FIG. 3A). The plunger device (FIG. 2B) with the self-detaching Gelare cap (FIG. 2B) may be utilized as a precautionary measure with the syringe casing (FIG. 3A). The self-detaching Gelare cap separates from the plunger device (FIG. 2B) and obstructs the existing opening through the syringe casing (FIG. 1A, 2A and/or 3A). The optional use of the Gelare capped plunger device (FIG. 2B) is a precautionary measure to an incomplete destruction of the Gelare tip (FIG. 3A) which houses the hypodermic needle (FIGS. 1A, 2A and/or 3A).

What is claimed is:

1. A self-destructing hypodermic syringe means comprising:
    a generally tubular hypodermic syringe casing consisting at least in part of a material solvable in at-least water and alcohol, the syringe casing having a distal end and a proximal end;
    a hypodermic syringe plunger means translatably movable through the syringe casing, including a tip means for sealing against interior surfaces of the syringe casing;
    tip means sealingly positioned in the proximal end of the syringe casing.
2. The means of claim 1 wherein a syringe casing is comprised at least partially of material soluble in substances from the set of water and alcohol based intraveneous medications.
3. The means of claim 1 wherein the syringe casing is made at least in part of collagen material.
4. The means of claim 1 wherein the syringe casing is made at least partially from L. Gelare material.
5. The means of claim 1 wherein the syringe plunger is made at least partially from self-destructing material.
6. The means of claim 5 wherein the self-destructing material is soluble in the solutions from the set of water and alcohol based intravenous based medications.
7. The means of claim 1 wherein the tip of the syringe plunger is made of elastomeric material.
8. The means of claim 7 wherein the elastomeric material is rubber.
9. The means of claimn 1 wherein the tip consists at least partially of self-destructing material.
10. The means of claim 9 wherein the self-destructing material in the tip is soluble in solutions from the set of water and alcohol based intravenous medications.
11. The device of claim 1 wherein the tip includes a needle means for penetration of a user's skin or musculature.
12. The means of claim 1 wherein the needle consists of selfdestructing material.
13. The means of claim 12 wherein the self-destructing material of the needle is soluble in the set of solutions of water and alcohol based intravenous medications.
14. The means of claim 12 wherein the needle is comprised of metal.
15. A self-destructing hypodermic device for one-time use with a solution comprised atleast in part by a degrading, debasing or solvent substance selected from the set of water and alcohol, comprising:
    a hypodermic syringe casing means for receiving and holding the solution, a tip disposed in one end of the casing and including a needle means for allowing passage of the solution and penetration in a user's skin; and
    a hypodermic syringe plunger means movable in the casing for drawing solution into the casing and dispelling solution from the casing through the tip means;
    any portion of the syringe casing, tip, and plunger being at least partially degradable, debaseable, or when contacted by the solution.
16. The means of claim 15 wherein any part of the syringe casing, tip and plunger is made of collagen.
17. A method for limiting hypodermic injections and withdrawals from a hypodermic syringe to one-time use comprising:
    making at least a portion of a hypodermic syringe means from a material which is self-destructing in the presence of the solution comprising the set of water and alcohol being intravenously injected or withdrawn.
18. The method of claim 17 further comprising the step of selecting the portion of the hypodermic syringe means which is at least partially self-destructable in the presence of the solution being intravenously injected or withdrawn to prevent a second use of the syringe means.

* * * * *